US009115884B2

(12) United States Patent
White (10) Patent No.: US 9,115,884 B2
(45) Date of Patent: Aug. 25, 2015

(54) HEAT ISOLATING TORCH

(75) Inventor: Ron White, North Prairie, WI (US)

(73) Assignee: Lamplight Farms, Inc., Menomonee Falls, WI (US)

( * ) Notice: Subject to any disclaimer, the term of this patent is extended or adjusted under 35 U.S.C. 154(b) by 728 days.

(21) Appl. No.: 13/460,390

(22) Filed: Apr. 30, 2012

(65) Prior Publication Data

US 2013/0288186 A1    Oct. 31, 2013

(51) Int. Cl.
*F21V 37/02* (2006.01)
*F21V 37/00* (2006.01)
*F23D 3/18* (2006.01)
*F21S 13/12* (2006.01)
*F23D 3/26* (2006.01)
*A61L 9/03* (2006.01)
*F21V 25/00* (2006.01)
*F21V 29/15* (2015.01)

(52) U.S. Cl.
CPC ............. *F21V 37/0004* (2013.01); *F21S 13/12* (2013.01); *F23D 3/18* (2013.01); *F23D 3/26* (2013.01); *A61L 9/037* (2013.01); *F21V 25/00* (2013.01); *F21V 29/15* (2015.01); *F21V 37/0016* (2013.01); *F21V 37/0058* (2013.01); *F21V 37/02* (2013.01)

(58) Field of Classification Search
CPC ......... F21L 17/00; F21L 19/006; F21L 23/00; F21L 27/00; F21V 37/02
USPC ........................................................ 431/310
See application file for complete search history.

(56) References Cited

U.S. PATENT DOCUMENTS

| | | | | |
|---|---|---|---|---|
| 65,229 | A | * | 5/1867 | Irwin ............................ 362/171 |
| 66,021 | A | * | 6/1867 | Heath ........................... 431/314 |
| 2,203,043 | A | | 4/1878 | Hillegass |
| 556,286 | A | * | 3/1896 | Schlicht ....................... 362/171 |
| 613,188 | A | | 10/1898 | Cadwallader et al. |
| 1,403,089 | A | * | 1/1922 | Lloyd et al. .................... 431/343 |
| 1,554,130 | A | * | 9/1925 | Sargeant ....................... 431/310 |
| 1,634,443 | A | * | 7/1927 | Bennett ........................ 431/307 |
| 1,705,877 | A | | 3/1929 | Ramsey |
| 1,732,708 | A | * | 10/1929 | Withrow et al. ............... 431/314 |
| 2,122,624 | A | | 7/1938 | Sauer |
| 2,182,143 | A | * | 12/1939 | Campbell ...................... 431/342 |
| 2,217,970 | A | | 10/1940 | Shearman et al. |
| 2,482,797 | A | * | 9/1949 | Quinnell et al. ................ 126/45 |
| 2,684,182 | A | | 7/1954 | Gey |
| 2,728,846 | A | * | 12/1955 | Prickett et al. ................ 362/181 |

(Continued)

FOREIGN PATENT DOCUMENTS

CA        2675817        10/2010
CN        2670364        1/2005

(Continued)

OTHER PUBLICATIONS

Pipe-Line Denmark, "Elipse Advanced Burning Control".

(Continued)

*Primary Examiner* — Jorge Pereiro
(74) *Attorney, Agent, or Firm* — Fellers, Snider, Blankenship, Bailey & Tippens, P.C.

(57) ABSTRACT

A device having a flame bowl surrounded by a first, inner shroud. The device includes a shell having a second, outer shroud on an upper portion thereof, the outer shroud circumscribing at least a portion of the first shroud, and a support supporting the flame bowl and the first shroud in a fixed relationship with respect to the outer shroud.

13 Claims, 8 Drawing Sheets

(56) References Cited

U.S. PATENT DOCUMENTS

| | | | | |
|---|---|---|---|---|
| 2,817,226 | A * | 12/1957 | Dickman | 431/146 |
| 2,836,043 | A | 5/1958 | Spethmann | |
| 3,154,065 | A * | 10/1964 | Bencoe | 126/44 |
| 3,225,756 | A * | 12/1965 | Bencoe | 126/9 R |
| 3,270,192 | A | 8/1966 | Watson | |
| 3,364,704 | A | 1/1968 | Bernstein | |
| 3,721,516 | A * | 3/1973 | Reese | 431/202 |
| 4,022,567 | A * | 5/1977 | Miyahara | 431/168 |
| 4,113,421 | A * | 9/1978 | Miyahara | 431/122 |
| D262,999 | S | 2/1982 | Spencer | |
| 4,477,247 | A | 10/1984 | Kumasaka | |
| D286,682 | S | 11/1986 | Greenlee | |
| 4,728,286 | A * | 3/1988 | Olsen | 431/320 |
| 4,734,833 | A * | 3/1988 | Schneeberger | 362/161 |
| 5,083,916 | A | 1/1992 | Glennon et al. | |
| 5,101,328 | A | 3/1992 | Hai | |
| 5,205,730 | A | 4/1993 | Capdeville | |
| 5,744,106 | A * | 4/1998 | Eagle | 422/306 |
| 5,807,093 | A | 9/1998 | Tendick, Sr. | |
| D404,507 | S | 1/1999 | Palmer et al. | |
| 5,902,101 | A | 5/1999 | Palmer et al. | |
| 5,938,430 | A | 8/1999 | Majerowski | |
| D433,763 | S | 11/2000 | Donato | |
| 6,231,336 | B1 * | 5/2001 | Chen | 431/291 |
| 6,345,978 | B1 | 2/2002 | Lu | |
| D456,917 | S * | 5/2002 | Kumar | D26/8 |
| 6,428,311 | B1 | 8/2002 | Bernardo | |
| D470,962 | S | 2/2003 | Chen | |
| 6,514,070 | B2 | 2/2003 | Lu | |
| D473,669 | S | 4/2003 | Hille et al. | |
| 6,562,302 | B1 * | 5/2003 | Hooks, II | 422/124 |
| 6,565,012 | B1 * | 5/2003 | Zaragoza et al. | 239/44 |
| 6,612,720 | B1 | 9/2003 | Beadle | |
| 6,663,258 | B1 | 12/2003 | Kanter | |
| D495,079 | S | 8/2004 | Mullen | |
| 7,073,920 | B2 * | 7/2006 | Konkle et al. | 362/161 |
| 7,156,653 | B1 | 1/2007 | DeMars | |
| D575,893 | S | 8/2008 | Castellucci et al. | |
| D589,188 | S | 3/2009 | Sabernig | |
| D591,896 | S | 5/2009 | Plonski et al. | |
| D611,637 | S | 3/2010 | Sabernig | |
| D611,640 | S | 3/2010 | Sabernig | |
| D625,850 | S | 10/2010 | Lu | |
| D659,871 | S | 5/2012 | Lee et al. | |
| 8,550,813 | B2 * | 10/2013 | Masterson et al. | 431/320 |
| 2001/0053504 | A1 | 12/2001 | Lu | |
| 2002/0080604 | A1 * | 6/2002 | Niermann | 362/173 |
| 2002/0102509 | A1 * | 8/2002 | Johnson | 431/321 |
| 2002/0164554 | A1 * | 11/2002 | Kisch et al. | 431/298 |
| 2003/0036030 | A1 * | 2/2003 | Doppelt | 431/316 |
| 2003/0103354 | A1 * | 6/2003 | Niermann | 362/317 |
| 2006/0147864 | A1 | 7/2006 | Donley | |
| 2006/0199129 | A1 | 9/2006 | Konkle, Jr. | |
| 2006/0251997 | A1 | 11/2006 | Schulte et al. | |
| 2007/0020572 | A1 | 1/2007 | Furner et al. | |
| 2007/0111149 | A1 * | 5/2007 | Matsuyama | 431/300 |
| 2007/0169409 | A1 | 7/2007 | Chang | |
| 2007/0190471 | A1 * | 8/2007 | Lin | 431/320 |
| 2009/0068608 | A1 | 3/2009 | Hansen | |
| 2009/0208890 | A1 * | 8/2009 | Chang | 431/291 |
| 2009/0220904 | A1 | 9/2009 | Masterson et al. | |
| 2010/0112503 | A1 | 5/2010 | Masterson | |
| 2010/0215549 | A1 * | 8/2010 | Corda | 422/122 |
| 2010/0255436 | A1 | 10/2010 | Lu | |
| 2010/0315022 | A1 * | 12/2010 | Schnitzer | 315/307 |
| 2011/0097676 | A1 | 4/2011 | Masterson et al. | |
| 2011/0239539 | A1 * | 10/2011 | Gatt | 48/61 |
| 2013/0129571 | A1 * | 5/2013 | Chiu | 422/126 |
| 2013/0330678 | A1 * | 12/2013 | Chen | 431/323 |

FOREIGN PATENT DOCUMENTS

| | | |
|---|---|---|
| CN | 201014219 | 1/2008 |
| CN | 201348155 | 11/2009 |
| FR | 2745362 | 8/1997 |
| WO | WO03106895 | 12/2003 |

OTHER PUBLICATIONS

Pipe-Line Denmark, "The Torch Master Brochure", Publisher: http://www.pipe-line.dk/pdf/English2007WEB.pdf.

European Patent Office, Extended European Patent Search for European Patent Application No. 13165624.1, Jul. 25, 2013, Published in: NL.

* cited by examiner

HEAT ISOLATING TORCH

FIELD OF THE INVENTION

This disclosure relates to liquid fueled torches in general and, more particularly, to a liquid fueled torch that isolates heated components from a user.

BACKGROUND OF THE INVENTION

Liquid fueled torches are utilized for a number of purposes such as lighting, decoration, and pest repellence. Some fuel and torch combinations operate at extremely high temperatures. This is particularly so where a large flame presence is desired, or where high temperatures are utilized to disperse repellants or other useful substances. For safety reasons, torches are rarely left unattended; and some users will want to place torches into storage as soon as possible after use. Sometimes it may also be desirable to relocate a torch that is operating, or has recently been operating.

What is needed is a system and method for addressing the above, and related, issues.

SUMMARY OF THE INVENTION

The invention of the present disclosure, in one aspect thereof, comprises a device having a flame bowl surrounded by a first, inner shroud. The device includes a shell having a second, outer shroud on an upper portion thereof, the outer shroud circumscribing at least a portion of the first shroud, and a support supporting the flame bowl and the first shroud in a fixed relationship with respect to the outer shroud.

In some embodiments, the support is perforated. An interior of the shell may have a lip providing a resting place for the support. In some embodiments the device has a slot defined in the lip, and a tab protruding from the support that interfits with the lip to retain the inner shroud in a fixed rotational relationship with respect to the outer shroud. The first and second shrouds may each be cut at an angle relative to the flame bowl such that each shroud has a high side and a low side. In some embodiments, the high sides and the low sides will be in substantially the same radial location with respect to the flame bowl.

The flame bowl may comprise a wick holder surrounded by a textured surface. The flame bowl may further comprise a threaded connection that interfits with a threaded neck of a fuel canister that is suspended from the flame bowl at least partially within the shell.

Some embodiments may include a snuffer cap sized to substantially cover the first shroud, and a retainer hook affixed to the shell for retaining the snuffer cap when not in use.

The invention of the present disclosure, in another aspect thereof, comprises a device having a flame bowl containing a wick in fluid communication with a fuel supply, a support attached to the flame bowl, and a torch body at least partially surrounding the support. The device has a first shroud in relative close proximity to the flame bowl and supported relative to the torch body by the heat dissipating support, and a second shroud at least partially surrounding the first shroud and supported by the torch body.

In some embodiments, each of the shrouds provides a relative high side and a relative low side and the high sides and low sides are fixed in the same rotational position relative to the flame bowl. A slotted lip may be provided by the torch body on an interior thereof, the slotted lip fitting with a tab on the support for maintaining the rotational positions of the shrouds.

A fuel canister containing the fuel supply may be attached to the flame bowl suspended at least partially within the torch body. The fuel canister may be connected to the flame bowl by a threaded fitting.

The support may comprise a heat dissipated perforated metal support. In another embodiment, the support is a heat isolating bridge. The flame bowl may be supported entirely below a level of the second shroud on the torch body. In another embodiment, the flame bowl is supported at least partially above a level of the second shroud on the torch body.

The invention of the present disclosure, in another aspect thereof, comprises a method including providing a flame bowl and a fuel supply suspended within a torch body by a heat dissipating support member, providing a first shroud in relative close proximity to the flame bowl, and providing a second shroud on the torch body at least partially surrounding the first shroud.

Some embodiments of the method include cutting the first and second shrouds at an angle relative to the flame bowl producing a high side and a low side on each shroud, and fixing the high side of each shroud at substantially the same rotational relationship with respect to the flame bowl. Some embodiments may also include providing a perforated metal support as the heat dissipating support member. The flame bowl may be texturized and provided with a threaded fitting thereon for retaining the fuel supply within the torch body.

DETAILED DESCRIPTION OF THE PREFERRED EMBODIMENTS

Figure 1:
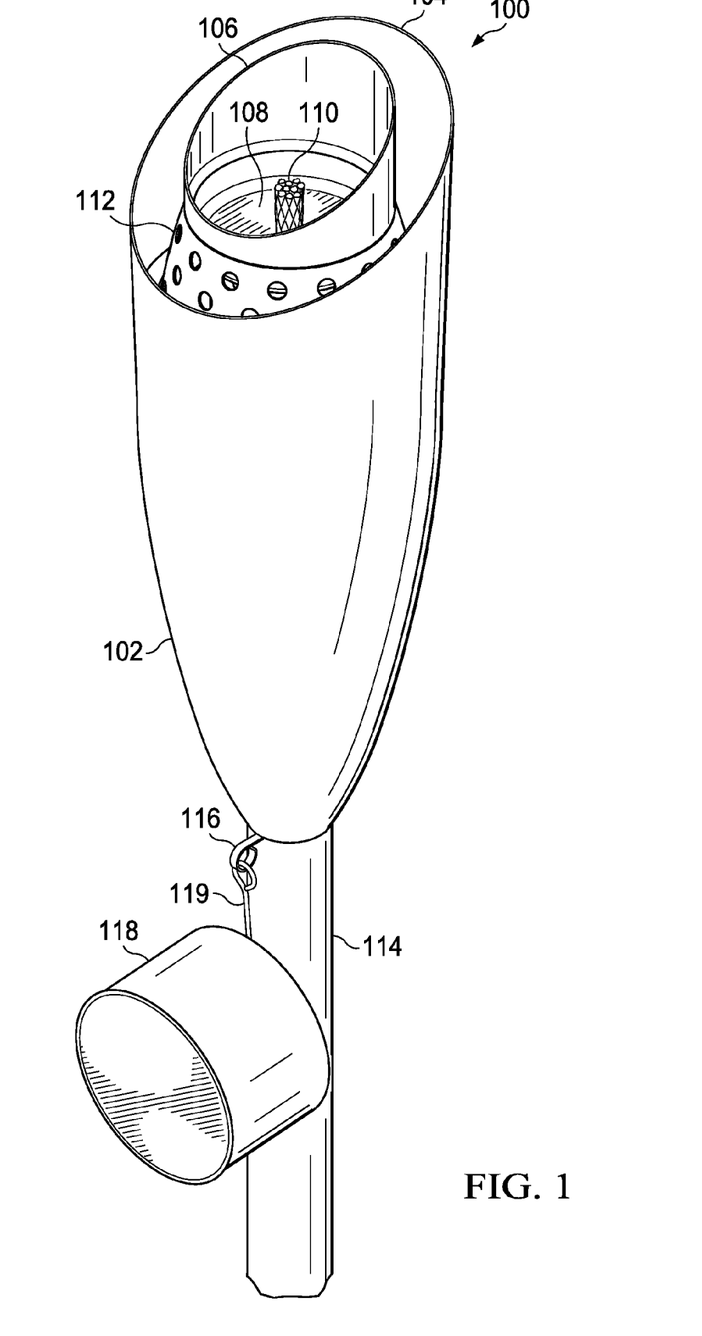
FIG. 1 is a front perspective view of one embodiment of a heat isolating torch according to the present disclosure.

Referring now to FIG. 1, a front perspective view of one embodiment of a heat isolating torch according to the present disclosure is shown. The torch 100 is referred to herein as being "heat isolating" due to the features described herein that reduce the temperature of the torch 100 at locations where a user would be likely to grasp or touch the torch 100. The torch 100 has a body 102 that may be made from steel or another metal. In some embodiments, the surface of the body 102 may comprise rolled steel and have a brushed or stainless appearance. Other embodiments may have a body 102 comprising a polymer or another suitable material. The body 102 may be cylindrical with a tapered lower portion. The body 102 also comprises an outer shroud 104. In some embodiments, the shroud 104 will be a continuous portion of the body 102.

The torch 100 may also comprise an inner shroud 106 surrounding a flame bowl 108. The flame bowl 108 and/or an interior portion of the inner shroud 106 may be texturized to promote a large and/or decorative flame from the wick 100. The inner shroud 106 and the flame bowl 108 may comprise steel or another heat resistant material. The wick 110 may be a durable fiberglass wick or another wick capable of withstanding high temperatures without being consumed.

A support 112 offsets the inner shroud 106 and flame bowl 108 from the body 102 of the torch 100. In some embodiments, the support 112 may be perforated in order to allow dissipation of heat as well as limiting heat that can be transferred from the inner shroud 106 and/or flame bowl 108 to the torch body 102. In some embodiments, the support 112 will comprise a heat resistant steel, and may comprise the same material as the flame bowl 108 and/or inner shroud 106.

The torch body 102 may have an attached pole 114 that may be placed in the ground or otherwise affixed to a secure surface. The pole 114 may be wooden, metal, plastic, or made from another material. In other embodiments, the torch 100 may be freestanding or configured for placement on a tabletop. A hook 116 may be provided on the body 102, the pole 114, or at the conjunction of the two, as shown. In the present embodiment, the hook 116 is configured to retain a snuffer cap 118, via an attached handle 119, when the cap 118 is not in use.

Figure 2:
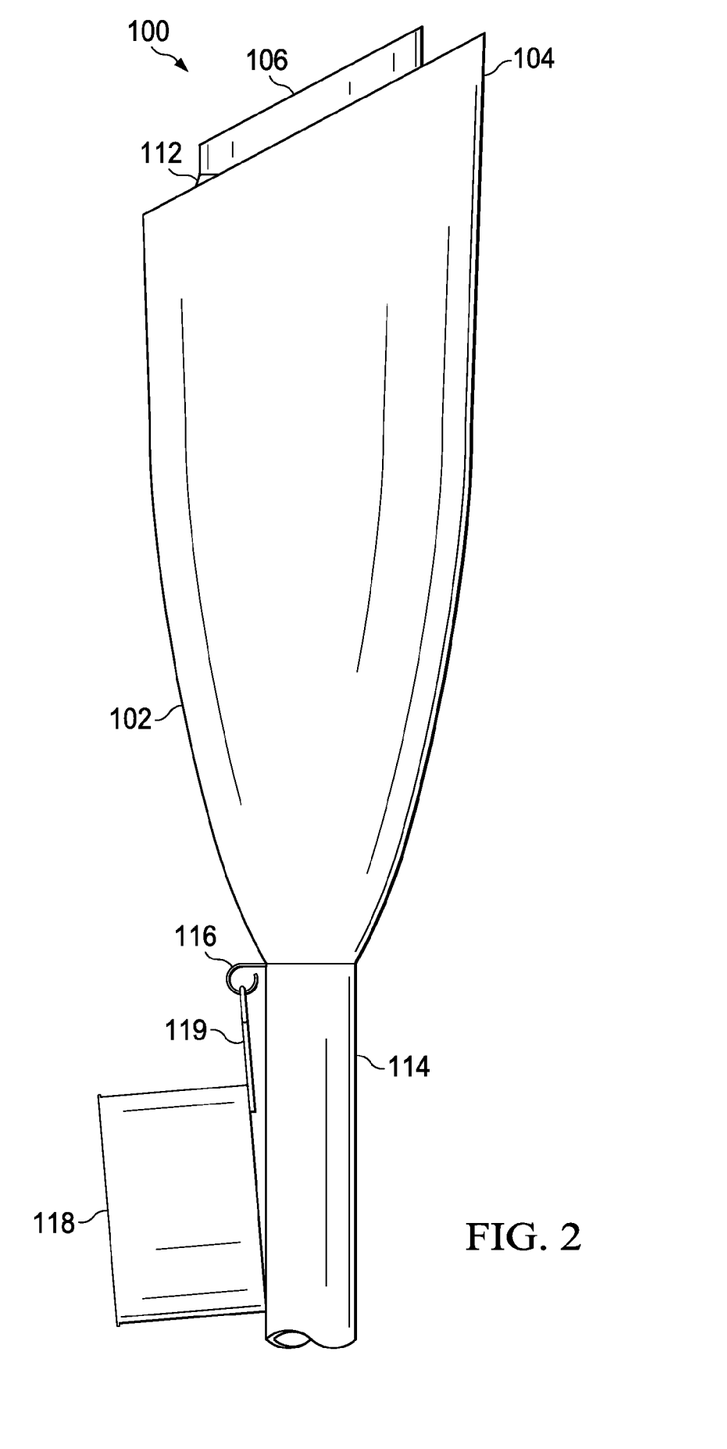
FIG. 2 is a side view of the torch of FIG. 1.

Referring now to FIG. 2, a side view of the torch 100 of FIG. 1 is shown. From the viewpoint of FIG. 2, it can be seen that the outer shroud 104 and inner shroud 106 are cut at an angle in the present embodiment. This configuration is decorative in some embodiments, but in other embodiments the configuration will allow for additional heat isolation and/or dispersion. It can also be seen that, in the present embodiment, the inner shroud 106 is raised only slightly above the level of the outer shroud 104.

Figure 3:
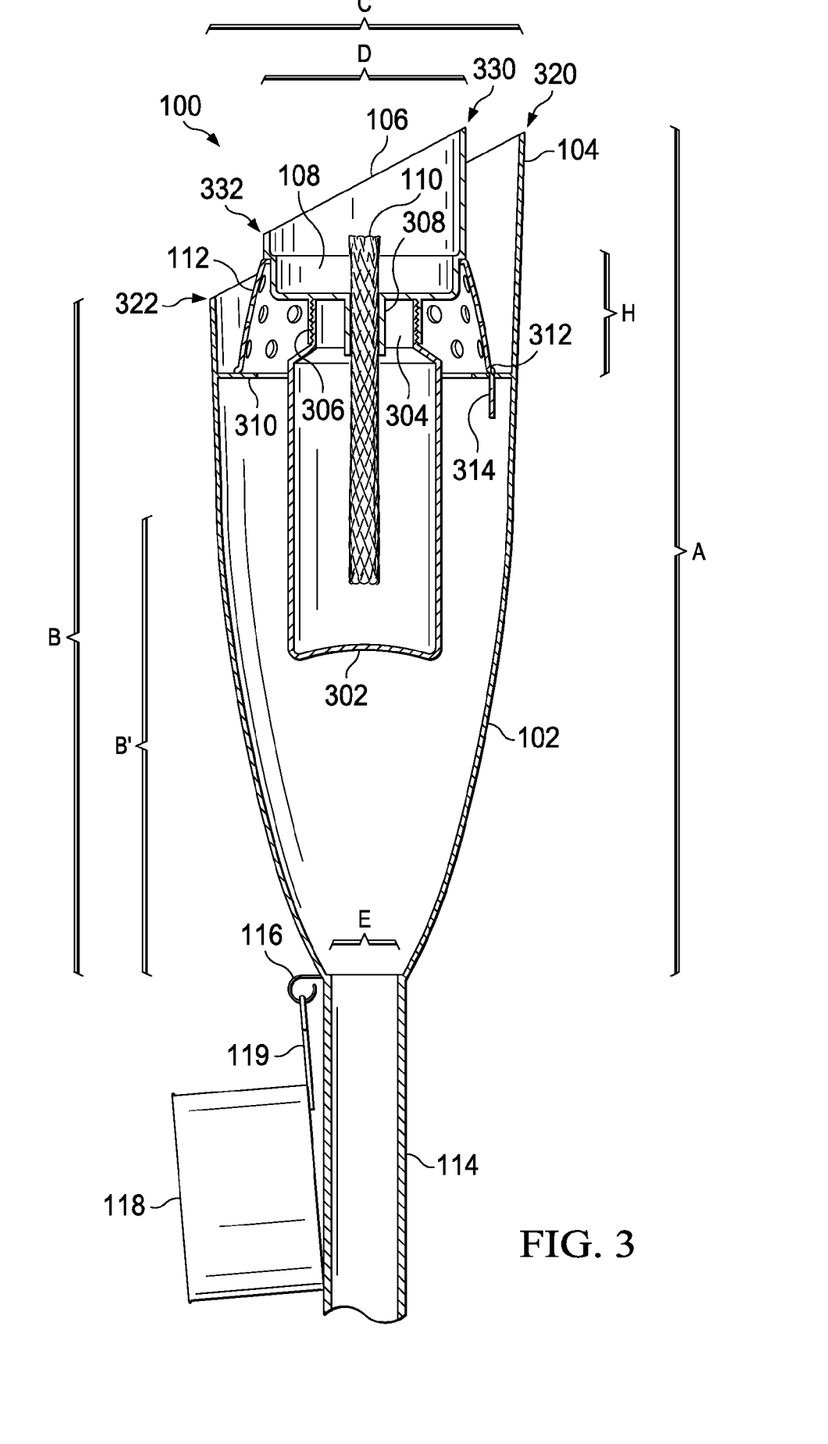
FIG. 3 is a side cutaway view of the torch of FIG. 1.

Referring now to FIG. 3, a side cutaway view of the torch of FIG. 1 is shown. FIG. 3 illustrates additional componentry within the torch 100 as well as certain dimensions of the particular exemplary embodiment shown. It can be seen that a fuel canister 302 is stored at least partially within the torch body 102. In the present embodiment, the fuel canister 302 has a threaded neck 304 that interfits with a threaded connector 306 on the lower portion of the flame bowl 108. In various embodiments, the canister may contain a supply of liquid torch fuel that may be imbued with other chemicals such as scents or repellants.

The flame bowl 108 can also be seen to provide a wick holder 308 that proceeds partially into the fuel canister 302 when the canister 302 is attached to the flame bowl 108. The perforated support 112 may join the flame bowl 108 and/or inner shroud 106 proximate a seam between the two components. The support 112 supports the inner shroud 106, the flame bowl 108, and the fuel canister 302, each at a predetermined height within the torch body 102 and/or outer shroud 104.

In the present embodiment, a lip 310 is provided on the interior of the torch body 102. The lip 310 provides a surface for engaging or supporting the support 112. In some embodiments, the lip 310 will define a slot or hole 312 at a certain location. A tab 314 that protrudes from the support 112 may interfit with the slot 314 in order to ensure that, when assembled, the components each maintain the proper relationship relative to one another. In the present embodiment, one function of the cooperating slot 312 and tab 314 is to ensure that an uppermost rim 320 of the outer shroud 104 can be easily aligned with an uppermost rim 330 of the inner shroud 106. Likewise, the slot 312 and tab 314 allow for easy alignment of a lowermost rim 322 of the outer shroud 104 with a lowermost rim 332 of the inner shroud 106.

As previously discussed, one result of constructing a liquid fuel burning torch according to the present disclosure is that the surfaces that are likely to be touched by a user can be kept at a relatively safe temperature. In some embodiments, the selection of the materials comprising the torch 100 will play a role. For example, stainless steel has good thermal conductive properties. However, dimensions of the device may also need to be considered in order to ensure isolation and/or dispersion of high temperatures. Therefore, a set of dimensions are given below in conjunction with the embodiment of FIG. 3. These dimensions may be used to produce a device of rolled steel with sufficient heat isolation and temperature dispersion properties to be safe for most users. However, this disclosure is not meant to be limited to the specific materials and dimensions given.

In the embodiment of FIG. 3, the overall height of the torch body 102, including the shroud 104, at the highest point is given by length A. In the present embodiment, this length is about 10.75 inches. A length B represents the shortest side of the torch body 102 in combination with the outer shroud 104. The length B in the present embodiment is about 8.75 inches. In the present embodiment, the overall diameter of the torch body 102 near the outer shroud 104 is given by dimension C, which is about 3.75 inches. The diameter of the flame bowl 108 and inner shroud 106 is given by dimension D, which in the present embodiment is about 2.5 inches. In the present example, the height H, of the support 112 is about 1.25 inches. Although the size of the torch body 102 where it attaches to the pole 114, length E, may be less critical to controlling temperature than some of the other dimensions, in the present embodiment it is about 1.5 inches.

Using the dimensions described above with respect to FIG. 3, when a common oil based torch fuel is utilized, the temperature at the rim 320 will be approximately 243° F. However, the temperature at the lower rim 322 of the outer shroud 104 will only be 164° F. Further down the torch body 102 temperatures continue to decrease. For example, in FIG. 3, a dimension B' is given, which is approximately ⅔ of the length of the dimension B. At this location, the temperature of the torch 100 when operating is only about 146° F.

It is understood that the inner shroud 106 is generally not safe for user contact when the torch 100 is, or had recently been, operating. However, the overall design and configuration of the torch 100 is meant, in some respects, to discourage a user from inadvertently touching the relatively hot inner shroud 106.

Figure 4:
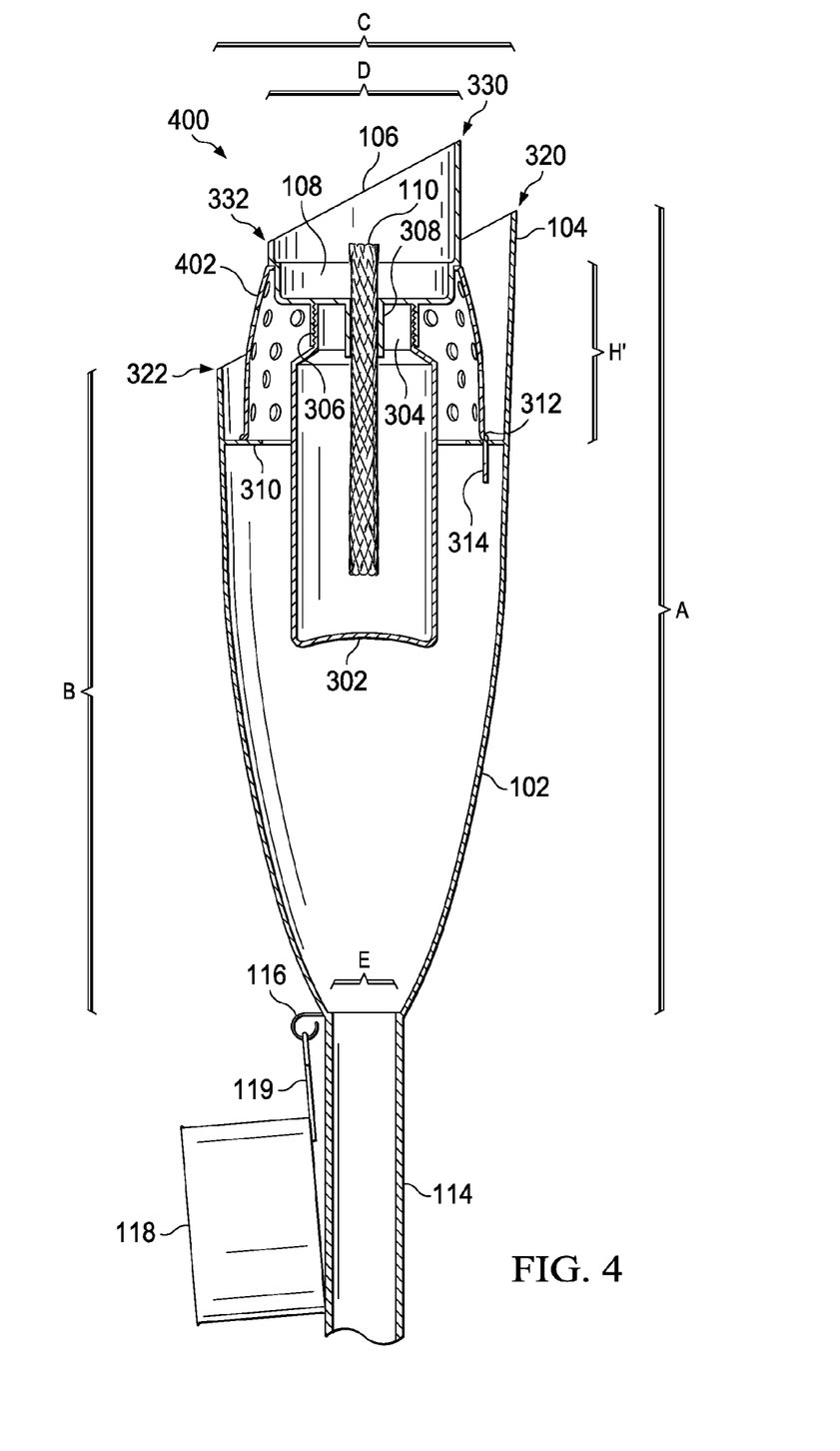
FIG. 4 is a side cutaway view of another embodiment of a heat isolating torch according to the present disclosure.

Referring now to FIG. 4, another embodiment 400 of a heat isolating torch is shown. The embodiment of FIG. 4 is substantially similar to the embodiment of FIG. 3, and shares most components and dimensions. However, in this embodiment, a perforated support 402 having height H' (that is greater than the height H of the support 112) is employed. In the present embodiment, H' is about 1.75 inches. This adjustment of the height of the support 402 elevates the flame bowl 108 at least partially above the level of the outer shroud 104. The inner shroud 106 is elevated substantially above the outer shroud 104. The increase in the height of the support 112 allows for additional heat dissipation from the support 112, as well as providing a longer thermal conductive pathway to the torch body 102. The result of this modification relative to the embodiment of FIG. 3 is that the operating temperature of the upper rim 320 of the outer shroud 104 has drops to 176° F. The operating temperature of the lower rim 322 of the shroud 104 is approximately 137° F. and decreases along the length B proceeding toward the pole 114.

Figure 5:
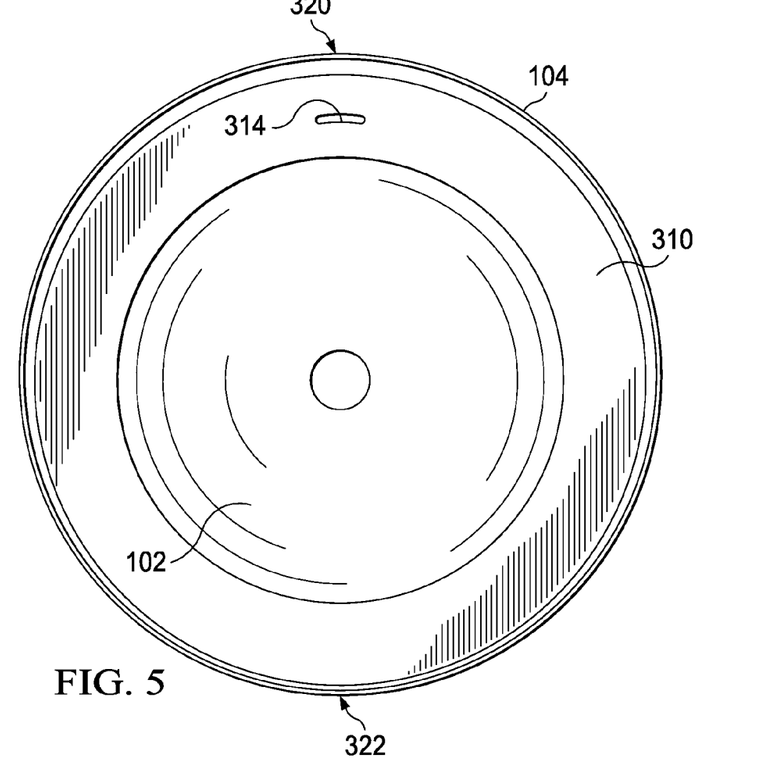
FIG. 5 is a top down view of the shell of the heat isolating torch of FIG. 1.

Referring now to FIG. 5, a top down view of the torch body 102 with the interior components removed is shown. Here, the lip 310 within the torch body 102 can be seen on the interior of the torch body 102. The location of the upper rim 320 and lower rim 322 of the attached outer shroud 104 can also be seen relative to the slot 314 defined in the lip 310.

Figure 6:
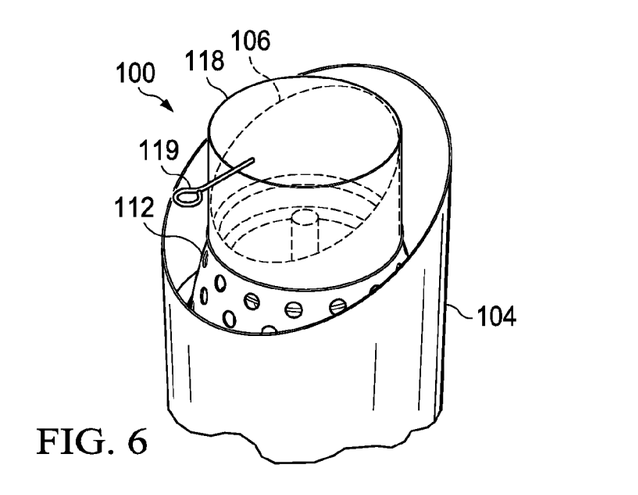
FIG. 6 is a perspective view of the torch of FIG. 1 with the snuffer cap on top.

Referring now to FIG. 6, a perspective view of a portion of the torch 100 is shown. Here, the snuffer cap 118 is shown in place over the inner shroud 106 and the flame bowl 108. It can be seen how the generally cylindrically-shaped snuffer cap 118 will substantially cover and enclose the inner shroud 106. When placed in the configuration shown, the snuffer cap 118 will safely extinguish any flame when the torch 100 is operational. The cap 118 is provided with a looped handle 119 that may also be used when placing the cap 118 into the position shown. This will minimize any chance that the user will contact the relatively hot inner shroud 106. Once any flames have been extinguished, the cap 118 may be removed and replaced on the storage hook 116, possibly using the handle 119.

Figure 7:
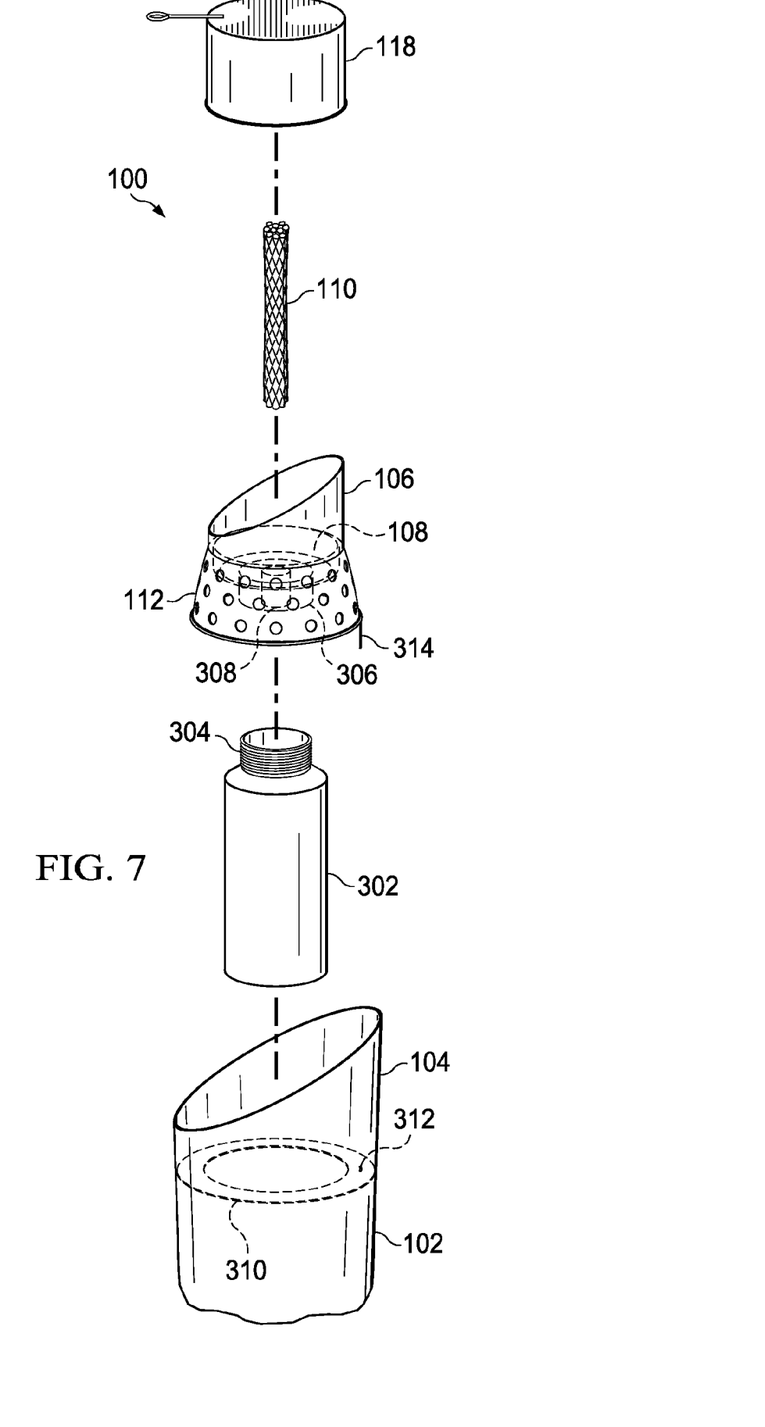
FIG. 7 is an exploded view of the torch of FIG. 1.

Referring now to FIG. 7, an exploded view of the torch 100 is shown. Here, the major components of the torch 100 can be seen separately. When assembling the torch 100, the fuel canister 302 may be attached to the flame bowl 108. The combination of the fuel canister 302, the flame bowl 108, the inner shroud 106, and the support 112 may then be lowered into the torch body 102. The tab 314 may be inserted into the slot 312 to ensure that the outer shroud 104 and inner shroud 106 are in correct alignment relative to one another. The wick 110 may be inserted into the wick holder 308. The wick holder 308 provides a friction fit to retain the wick 110 at the appropriate height. Depending upon the embodiment, the wick 110 may be extended further within the flame bowl 108 to produce greater flame, but at the expense of greater fuel consumption. As previously described, the snuffer cap 118 may be placed over the flame bowl 108 and inner shroud 106 to extinguish an operating torch. When not in use, the cap 118 may be stored on the hook 116.

Figure 8:
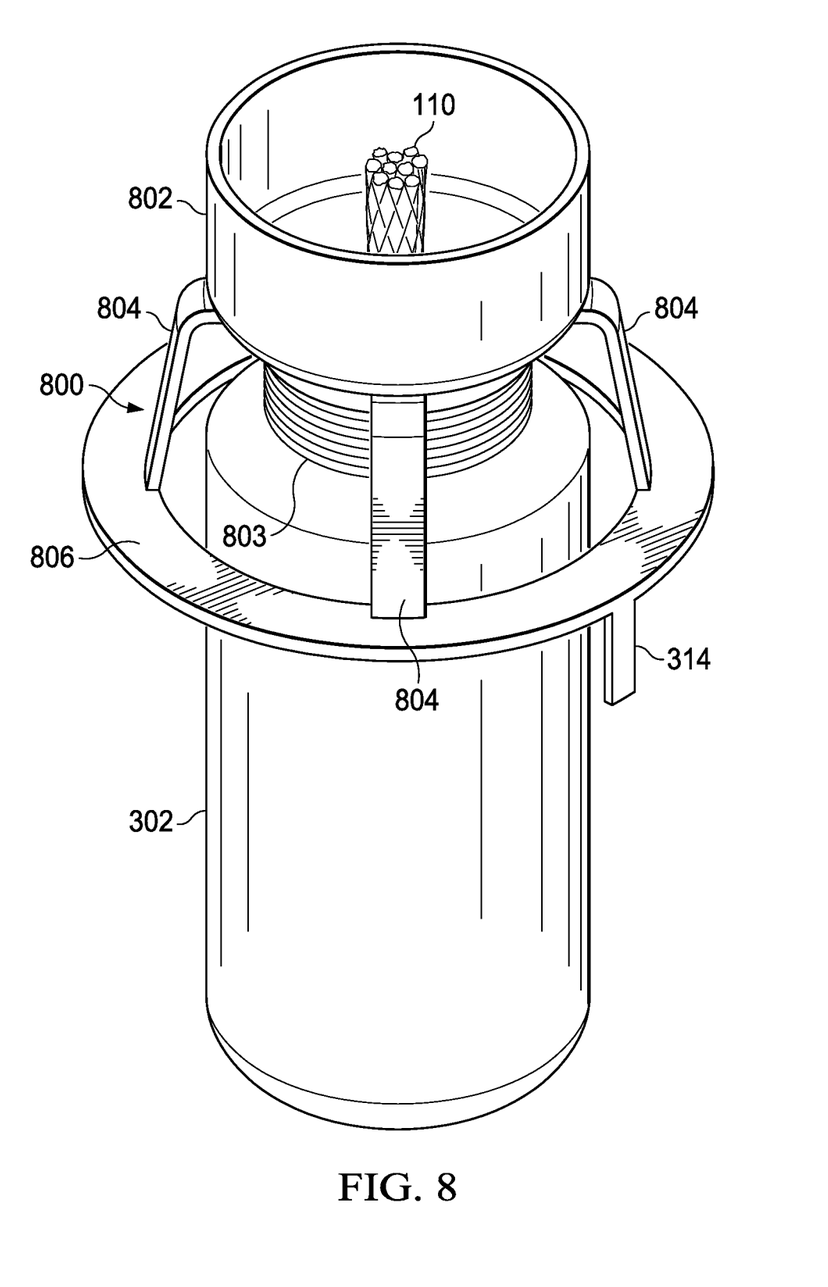
FIG. 8 is a perspective view of a flame bowl support for use with the torch of FIG. 1.

In the previously described embodiments, the supports 112/402 were described as being heat dissipating supports. The supports 112/402, in some embodiments, comprise a metal having a relatively high heat conductance, but also being perforated to dissipate absorbed heat. In other embodiments, an approach may be used to isolate the heat generated in the flame bowl from the rest of the structure. Referring now to FIG. 8, a perspective view of a flame bowl support 800 for use with the torch of FIG. 1 is shown. This support 800 comprises a plurality of legs 804 attached to a ring 806. The ring 806 may sit on the lip 310 (FIG. 3) when the torch 100 is assembled. The ring 806 may also be provided with the tab 314 for fitting into the slot 312 of the lip 310.

In some embodiment, the legs 804 will serve to isolate a flame bowl 802 from the rest of the torch 100. In some embodiments, the legs 804 may be metal, but where additional heat isolation is sought, the legs 804 may comprise a ceramic, resin, or other material having a low thermal conductivity.

The fuel canister 302 is shown attached to a flame bowl 802 via threaded fitting 803. Here the flame bowl 802 is relatively large compared to the wick 110, which may result in a large flame appearance. The flame bowl 802 may comprise the same material as the support 800 or may be made from a different material. In can also be seen that the flame bowl 802 is generally cylindrical in shape rather than having a tapered appearance (e.g., a high side and a low side). It is understood that the tapered appearance of the previously described embodiments is only for illustration, and that inner and outer shrouds and/or flame bowls may have a differing appearances than illustrated. In some embodiments, the flame bowl 802 may be textured or coated on an interior thereof to promote a large flame and/or flame effects.

Figure 9A:
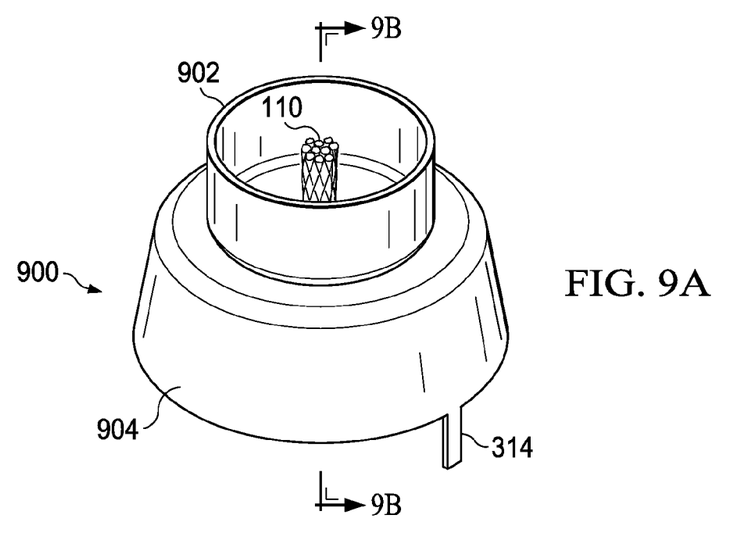
FIG. 9A is a perspective view of another flame bowl support for use with the torch of FIG. 1.

FIG. 9A is a perspective view of another flame bowl support 900 for use with the torch 100 of FIG. 1. Here, the support 900 comprises a non-perforated cone 904 that rests upon lip 310 (FIG. 3) and supports a flame bowl 902. The support 904 may provide a tab 314 for fitting slot 312. The flame bowl 902 may be generally cylindrical in shape or may have another outline. The cone 904 may comprise a metal, a ceramic, a resin, or another suitable material. In one embodiment, the material for the cone 904 may be chosen for its heat isolation properties.

Figure 9B:
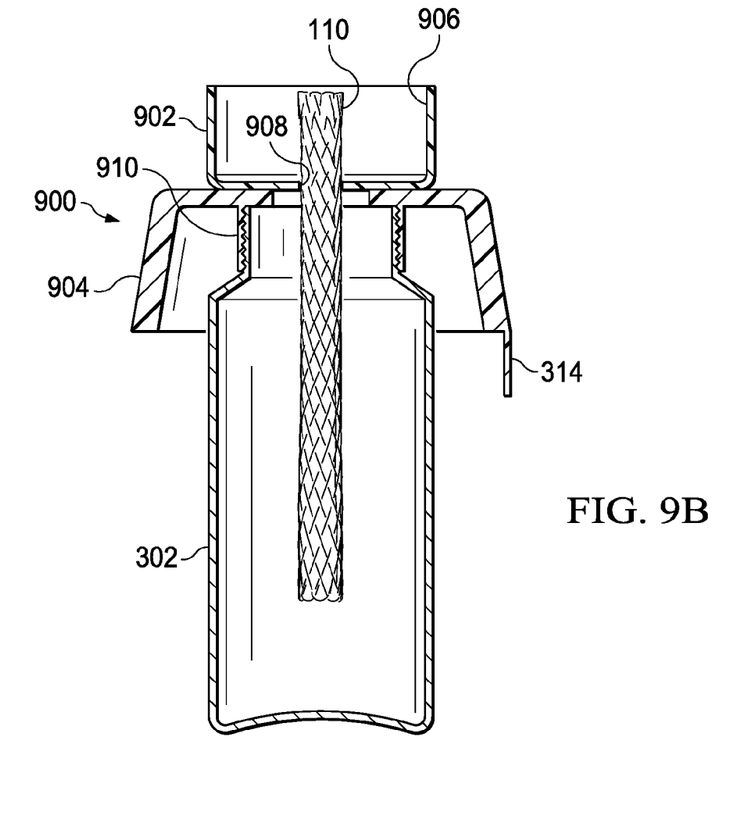
FIG. 9B is a side cutaway view of the support of FIG. 9A.

FIG. 9B is a side cutaway view of the support 900 of FIG. 9A. Here a threaded fitting 910 can be seen. The fitting 910 may be used to attach the fuel reservoir 301 (FIG. 3) to the cone 904 and/or base of the flame bowl 902. The flame bowl 902 may comprise the same material as the support 900, or may comprise a different material. An interior 906 of the flame bowl 902 may be textured or coated to promote a large flame and/or flame effects. A wick holder or wick passage 908 may be defined through the flame bowl 906 and/or support 900 for the wick 110.

* * *

Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art. Such changes and modifications are encompassed within the spirit of this invention as defined by the claims.

What is claimed is:

1. A device comprising:
   a flame bowl surrounded by a first. inner shroud:
   a shell having a second, outer shroud on an upper portion thereof, the outer shroud circumscribing at least a portion of the first shroud;
   a support supporting the flame bowl and the first shroud in a fixed relationship with respect to the outer shroud;
   a lip on an interior of the shell. the lip providing a resting place for the support;
   a slot defined in the lip;
   a tab protruding from the support that interfits with the lip to retain the inner shroud in a fixed rotational relationship with respect to the outer shroud; and
   wherein the first and second shrouds are each cut at an angle relative to the flame bowl such that each shroud has a high side and a low side, the high sides and the low sides being in substantially the same radial location with respect to the flame bowl.

2. The device of claim 1, wherein the support is perforated.

3. The device of claim 1, wherein the flame bowl further comprises a wick holder surrounded by a textured surface.

4. The device of claim 1, wherein the flame bowl further comprises a threaded connection that interfits with a threaded neck of a fuel canister that is suspended from the flame bowl at least partially within the shell.

5. The device of claim 1, further comprising a snuffer cap sized to substantially cover the first shroud.

6. The device of claim 5, further comprising a retainer hook affixed to the shell for retaining the snuffer cap when not in use.

7. A device comprising:
a flame bowl containing a wick in fluid communication with a fuel supply;
a support attached to the flame bowl;
a torch body at least partially surrounding a heat dissipating support;
a first shroud in relative close proximity to the flame bowl and supported relative to the torch body by the support; and
a second shroud at least partially surrounding the first shroud and supported by the torch body;
wherein each of the shrouds provides a relative high side and a relative low side and the high sides and low sides are fixed in the same rotational position relative to the flame bowl; and
wherein the torch body provides a slotted lip on an interior thereof, the slotted lip fitting with a tab on the support for maintaining the rotational positions of the shrouds.

8. The device of claim 7, further comprising a fuel canister containing the fuel supply and attached to the flame bowl suspended at least partially within the torch body.

9. The device of claim 8, wherein the fuel canister is connected to the flame bowl by a threaded fitting.

10. The device of claim 7, wherein the support comprises a heated dissipating perforated metal support.

11. The device of claim 7, wherein the support comprises a heat isolating bridge.

12. The device of claim 7, wherein the flame bowl is supported entirely below a level of the second shroud on the torch body.

13. The device of claim 7, wherein the flame bowl is supported at least partially above a level of the second shroud on the torch body.

* * * * *